United States Patent [19]

Lee et al.

[11] Patent Number: 5,489,575
[45] Date of Patent: Feb. 6, 1996

[54] POLYPEPTIDES AND THEIR USE

[75] Inventors: Jong-Youn Lee, Enskede; Hans G. Boman, Odengatan 23, S-11424 Stockholm; Viktor Mutt, Solna; Hans Jörnvall, Sundbyberg, all of Sweden

[73] Assignee: Hans G. Boman, Stockholm, Sweden

[21] Appl. No.: 162,052

[22] PCT Filed: Jun. 10, 1992

[86] PCT No.: PCT/SE92/00394

§ 371 Date: Jun. 2, 1994

§ 102(e) Date: Jun. 2, 1994

[87] PCT Pub. No.: WO92/22578

PCT Pub. Date: Dec. 23, 1992

[30] Foreign Application Priority Data

Jun. 14, 1991 [SE] Sweden ................... 9101838

[51] Int. Cl.⁶ .............. A61K 38/00; C07K 5/00; C07K 7/00; C07K 17/00
[52] U.S. Cl. ............................. 514/12; 530/324
[58] Field of Search ................ 530/324; 514/12

[56] References Cited

U.S. PATENT DOCUMENTS 5,096,886  3/1992  Boman et al. ................ 514/12

FOREIGN PATENT DOCUMENTS 0403458   12/1990  European Pat. Off. .
WO89/01486  2/1989  WIPO .

OTHER PUBLICATIONS

Proc. Natl. Acad. Sci USA, "Antibacterial Peptides from Pig Intestine: Isolation of a Mammalian Cecropin", Jong–Youn Lee et al., vol. 86, pp. 9159–9162, Dec. 1989.

Primary Examiner—Jill Warden
Assistant Examiner—Sheela J. Huff
Attorney, Agent, or Firm—Burns, Doane, Swecker & Mathis

[57] ABSTRACT

Polypeptides comprising the following amino acid sequence: Arg-Arg-Arg-Pro-Arg-Pro-Pro-Tyr-Leu-Pro-Arg-Pro-Arg-Pro-Pro-Pro-Phe-Phe-Pro-Pro-Arg-Leu-Pro-Pro-Arg-Ile-Pro-Pro-Gly-Phe-Pro-Pro-Arg-Phe-Pro-Pro-Arg-Phe-Pro; pharmaceutical compositions containing such polypeptides; and a method of inhibiting bacterial growth using such polypeptides.

12 Claims, 1 Drawing Sheet

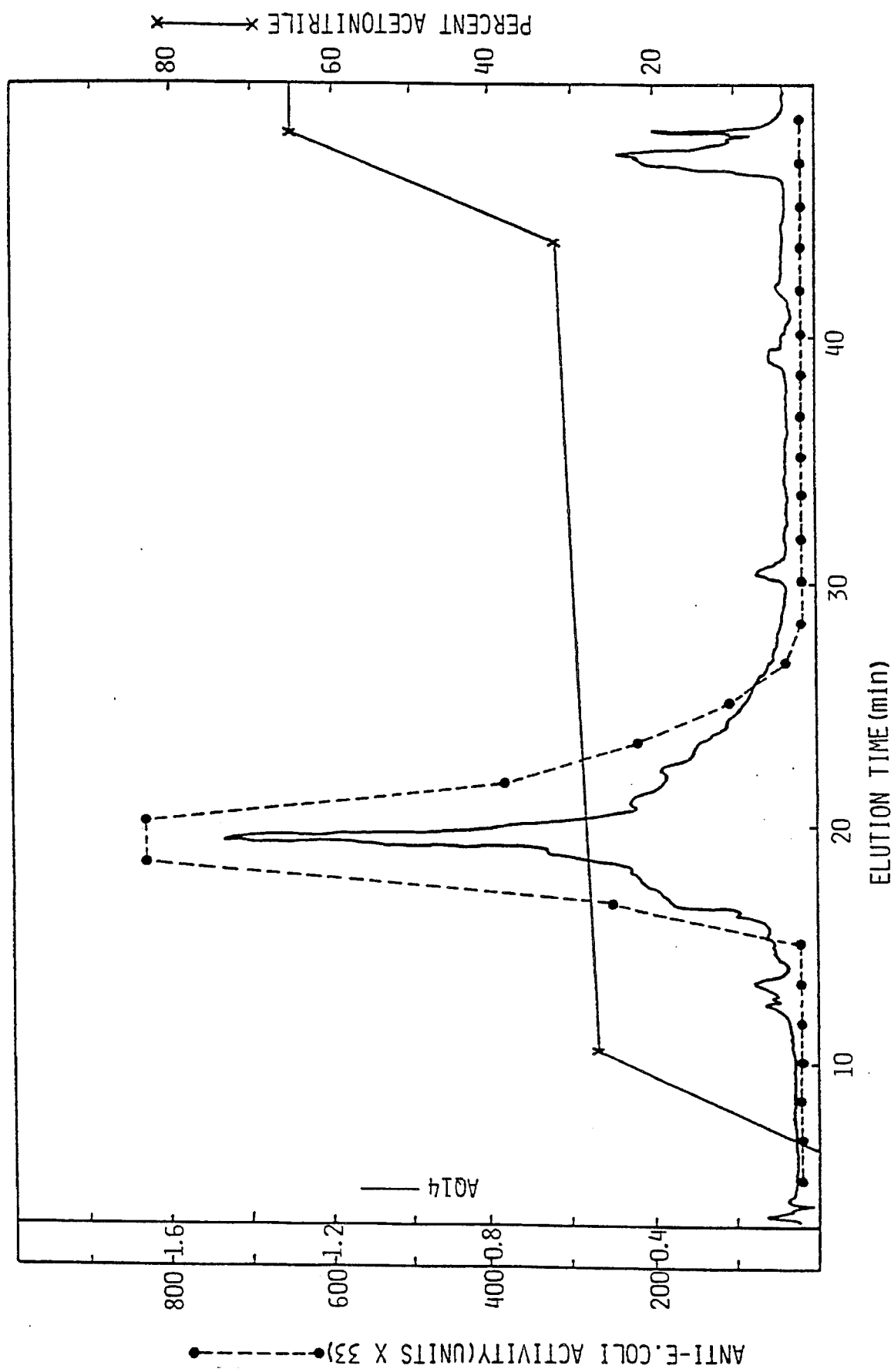

POLYPEPTIDES AND THEIR USE

The present invention relates to new polypeptides having bacteriocidal activity in that they are capable of killing certain bacteria, particularly gram-negative ones. The invention also covers pharmaceutical compositions and methods of use for the inhibition of bacterial growth.

The small intestine is an important endocrine organ and a number of physiologically active peptides have been initially isolated from porcine tissue (Mutt, V., Chemica Scripta 26B, 191–207 (1986)). During normal healthy conditions, the upper part of the small intestine contains few bacteria. Below the duodenum the concentration of bacteria progressively increases until the maximum, $10^{11}$ bacteria per g of feces, is reached in the large intestine. It is remarkable that such a mass of bacteria can coexist with a delicate host organ. Small basic peptides called cecropins play an important role in insect immunity (Boman, H. G. & Hultmark, D., D.Ann.Rev.Microbiol. 41, 103–126 (1987)) and structurally unrelated peptides called magainins (Zasloff, M., Proc.Natl. Acad. Sci. USA, 84, 5449–5453 (1987)) protect the frog skin from infections. Another group of antibacterial peptides, the defensins were first isolated from mammalian granulocytes (Selstedt, M. E., Szklarek, D. & Lehrer, R. I. Infect. Immun. 45, 150–154 (1984)) and neutrophils (Selstedt, M. E., Brown, D. M., DeLange, R. J., Harwig, S. S. & Lehrer, R. I., J.Biol. Chem 260, 4579–4584 (1985)) and recently also from insects (Matsuyama, K. & Natori, S. J.Biol.Chem. 263, 17112–17116 (1988); Lambert, J. et al. Proc.Natl.Acad. Sci. USA 86, 262–266 (1989)). In addition, bovine neutrophils have been found to contain bactenecins (Romeo, D., Skerlavaj, B., Bolognesi, M & Gennaro, R. J.Biol.Chem. 263, 9573–9575 (1988), another small basic peptide. Both defensins and the small bactenecin contain one or more disulfide bridges while cecropins and magainins are cysteine-free. Frank et al (J. Biol. Chem. 265:18871–18874) have described two large bactenicins with high contents of proline and arginine and without cysteine.

The present invention has for an object to provide new bactericidal polypeptides capable of inhibiting bacterial growth, in particular the growth of gram negative bacteria. In this disclosure the term "inhibiting" also includes the killing of bacteria.

Another object of the invention is to provide compositions containing as an active constituent such polypeptides.

Yet another object of the invention is to provide a method of treatment directed to inhibition of bacterial growth in animals, in particular mammals including man.

For these and other objects which will be clear from the following disclosure the invention provides a polypeptide having the amine acid sequence [SEQ ID NO.:1]:

Arg-Arg-Arg-Pro-Arg-Pro-Pro-Tyr-Leu-Pro-Arg-Pro-Arg-Pro-Pro-Phe-Phe-Pro-Pro-Arg-Leu-Pro-Pro-Arg-Ile-Pro-Pro-Gly-Phe-Pro-Pro-Arg-Phe-Pro-Pro-Arg-Phe-Pro, and the invention also includes functional derivatives such as a few conservative amine acid replacements and the C-terminal amide.

The polypeptide of the present invention and its functional derivatives are all therapeutically useful, particularly as antibacterial agents, Thus, they are capable of inhibiting growth of bacteria or killing bacteria, in particular gram-negative bacteria making them useful for different therapeutic purposes. This will be further illustrated by specific examples which are given below.

The active polypeptide according to the present invention can be formulated for use in human or veterinary medicine for therapeutic or profylactic use. The active preparations are normally administered orally, rectally or parenterally, such as by injection in the form of a pharmaceutical preparation or composition comprising the active constituents in combination with a pharmaceutically acceptable carrier which may be solid, semi-solid or liquid, or contained in a capsule, such as when orally administered. The administration may also take the form of topical application. As examples of pharmaceutical preparations there may be mentioned tablets, drops, solutions and suppositories. Usually, the active constituent constitutes the minor part of the preparation, such as from about 0.1 to about 50% thereof based on weight.

In order to prepare pharmaceutical compositions in the form of dose units for oral application the polypeptide of the invention can be mixed with a solid, pulverulent or other carrier, for example, lactose, saccharose, sorbitol, mannitol, starch, such as potato starch, corn starch, millopectine, cellulose derivative or gelatine, and may also include lubricants, such as magnesium or calcium stearate, or polyethylene glycol waxes compressed to the formation of tablets or bodies for dragées. The dose units may also be presented in a coated form of enteric type.

By using several layers of the carrier or diluent tablets operating with slow release can be prepared.

Liquid preparations for oral application or for injection can be made in the form of elixirs, syrups or suspensions, for example solutions containing from 0.1 to 20% by weight of active substance, sugar and a mixture of ethanol, water, glycerol, propyleneglycol and possibly other additives of a conventional nature.

The dose by which the active constituent is administered may vary within wide limits and is dependent on different factors, such as the seriousness of the disorder, the age and the weight of the patient and can be adjusted individually.

The invention also covers a method for therapeutic treatment of animals, such as mammals including man, said method comprising the step of administering a polypeptide as described above or a functional derivative thereof in an amount capable of killing bacteria or inhibiting bacterial growth in said animal.

The present invention will now be further exemplified by specific examples which, however, are not to be construed as limiting the scope of the invention otherwise than according to the appended claims.

BRIEF DESCRIPTION OF THE FIGURE

The FIGURE depicts the antibacterial activity (against *E coli*) of eluates containing the subject polypeptide eluted with acetonitrile as a function of elution time.

EXAMPLE 1

Preparation of a Peptide Concentrate

A concentrate of thermostable intestinal peptides was prepared from pig small intestine essentially as described elsewhere (Mutt, V. Arkiv Kemi 15, 69–74 (1959); Mutt, V. in Gut Hormones (ed. Bloom, S. R.), pp 21–27, (Churchill Livingstone, Edinburgh, 1978).

Briefly, the uppermost meter of the intestine was immersed for 8± 1 min into boiling water and then cooled on ice and frozen. The frozen material was minced and extracted at 0°–15° C. with 0.5M acetic acid for 12 h and the mixture filtered with suction (with the aid of "Hyflo Super-Col", 30 g per liter suspension). Peptides were adsorbed from the filtrate to alginic acid and the alginic acid carrying the peptides was washed in turn with 0.005M HCl, 95% ethanol (to remove fats) and 0.005M HCl again. The peptides were eluted with 0.2M ice-cold HCl and the pH of the eluate was brought to 3.5±0.1 with sodium acetate. Peptides were then precipitated by saturating the eluate with NaCl, and the precipitate was collected by suction filtration. The amount by weight of the precipitate (wet weight) is about one thousandth of that of the boiled intestinal tissue.

The concentrate was dissolved at room temperature to a 10% w/v solution in water. Two volumes of 95% ethanol were added to the solution, and the (apparent) pH (as measured with a glass electrode) or it was brought to 7.5±0.1 with NaOH (1M NaOH:EtOH 1:2). A precipitate formed and was removed by filtration. To the clear solution one volume of 95% ethanol precooled to −20° C. was added and the suspension was kept at this temperature for 24 h whereupon it was filtered. The peptides were recovered from the filtrate in aqueous solution and precipitated at pH 3.5±0.1 by saturation of the solution with NaCl. The precipitate, collected by suction filtration, weighed about 10% of that or the concentrate taken for its preparation. It was dissolved in 0.2M AcOH and chromatographed in this solvent on Sephadex G-25 fine. The second half by volume of the peptide-containing eluate from this chromatography was saturated with NaCl and the precipitate collected by suction filtration. Its weight was about 40% of that of the peptide precipitate taken for this chromatography. It was dissolved in water, the pH of the solution was adjusted to 4± 0.1 whereupon the peptides were reprecipitated with NaCl and the precipitate collected by suction (there was no significant difference in weight of the material before and after reprecipitation). The reprecipitated material was extracted with methanol (50 ml/g) and the MeOW-insoluble fraction was collected by suction filtration and washed on the filter with ether. The ether was evaporated in vacuo. The weight of the dry material was about 15% of that of the peptide precipitate taken for extraction with MeOH.

EXAMPLE 2

Purification of Concentrate

As a starting material for the purification there was used the concentrate resulting from Example 1. The concentrate (1, 5 g) was dissolved in 80 ml ammonium formate, pH 6.4, and treated with 30 ml of DEAE Sepharose, batch-wise.

Step 1: Chromatography on CM-Sepharose CL-6B (56 ml column, equilibrated with 0.1 H ammonium formate. pH 8.4). Elution was initially carried out with 0.1M ammonium formate (about 2100 ml) to a low extinction and then gradient elution was performed using 0.1–0.85M ammonium acetate, pH 5.2 (300+ 300 ml). The activity leaves as an integral peak having a maximum at 0.38M, specific activity 30–40 units/µg. (1 unit is defined as the activity of 1 ng of cecropin A.) The fraction showing the highest antibacterial activity was chosen for further purification.

Step 2: Further purification of pSCMC fraction

PSCMC fraction was dissolved in 8 mg/ml H$_2$O. 50 µl of sample (0.4 mg) was mixed with 450 µl 0.1% TFA in water and applied on a FPLC coupled Pep RPC HR5/5 (Pharmacia). The column was washed with 0.1% TFA in H$_2$O for 10 min. at a flow rate of 0.5 ml/min. Then the acetonitrile concentration was raised to 27% in 5 min. The active material was eluted with a gradient of 27%–32% acetonitrile in 34 min. An aliquot (50 µl or 100 µl) of each fraction was dried in the Speedvac and dissolved in 10 µl H$_2$O and 3 µl was used in an antibacterial assay.

Result: The active material was eluted at 28.5% acetonitrile under the chosen gradient profile. On the FIGURE there is shown a diagram on antibacterial activity (*E. coli*) as a function of elution time. As a test sample there was used 0.4 mg of the purified active fraction in 50 µl H$_2$O mixed with 450 µl of 0.1% TFA in H$_2$O. The sample was applied to Pep RPC HR5/5 coupled to FPLC. The elution program was as follows:

| Time | % acetonitrile |
|---|---|
| 0 | 0 |
| 10 | 0 |
| 15 | 27 |
| 49 | 32 |
| 54 | 65 |

EXAMPLE 3

Antibacterial assay

The antibacterial activity of the polypeptide of this invention was determined by inhibition zone assay as described by Hultmark et al. (Hultmark, D., Engström, A., Anderson, K., Steiner, H., Bennich, H. and Boman, H. G. (1983). Insect immunity. Attacins, a family of antibacterial proteins from *Hyalophora cecropia*. EMBO J. 2, 571–576).

Log-phase bacteria were grown to a density of 100 units on a Klett-summerson photoelectric colorimeter. They were diluted 50 times with LB medium and 50 µl of the bacteria suspension was mixed with 6 ml of 1.0% agarose in LB medium (w/v) and poured on the petri dishes (Falcon 1001 Optilux) with inner diameter 8.65 cm. For *E. coli* this procedure will give about 2×10$^5$ bacteria per plate.

The plates were left for 1 hour at room temperature, and holes with 3 mm diameter were made on the solidified agarose. 100 µl of fractions were dried in a speedvac and dissolved in 10 µl H$_2$O, of which 3 µl was applied to the holes. After 30 min diffusion time the plates were incubated at 30° C. overnight. The diameter of the inhibition zones were measured and the relative unit activity was calculated from a standard curve which was constructed on varying amount of Cecropin A versus activity. One microgram of Cecropin A corresponds to 1000 units of activity.

| The anti-*E. coli* activity of PS CMC fractions | |
|---|---|
| Fraction No. | Specific activity (units/µg) |
| PS CMC Fr. I | 0.5 |
| PS CMC Fr. II | 0.7 |
| PS CMC Fr. III | 1.4 |
| PS CMC Fr. IV | 2.0 |
| PS CMC Fr. V | 14.0 |
| PS CMC Fr. VI | 84.0 |
| PS CMC Fr. VII | 100.0 |

The anti-*E. coli* activity of fractions collected from reverse phase chromatography of PS CMC Fr. VII on a FPLC coupled PepRPC HR5/5 column.

| Fraction No. | Unit activity/fraction |
|---|---|
| Fr. 1–8 | activity not detectable |
| Fr. 9 | 8400 |

| Fr. 10 | 28000 |
| Fr. 11 | 28000 |
| Fr. 12 | 13000 |
| Fr. 13 | 7300 |
| Fr. 14 | 3500 |
| Fr. 15 | 1100 |
| Fr. 16–30 | activity not detectable |

In this test 400 µg PS CMC Ft. VII was applied to the column.

| Organism | Strain | Max zone (mm) | LC value (µM) |
|---|---|---|---|
| Staphylococcus aureus | Cowan 1 | 3,7 | 200 |
| Streptococcus pyrogenes | — | 14,9 | 2 |

The maximum concentration of PR-peptide was 2,5 mM and 3 µl was applied to each well in thin agarose plates seeded with test bacterium. LV values are obtained from a dilution serie and is the lowest concentration giving killing (Muirmark, D., Engström, A., Anderson, K., Steiner, H., Bennich, H. and Boman, H. G. (1983))

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 39 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro
            35

EXAMPLE 4

Example 3 was repeated by using *Bacillus megaterium* for measuring the antibacterial activity of the present polypeptide. The experiment has shown that *Bacillus megaterium* is more sensitive than *E. coli* to the peptide, the average activity of the polypeptide being about 3 times higher than in relation to *E. coli*.

EXAMPLE 5

Inhibition Zone Assay of PR-peptide on Different Bacteria

| Organism | Strain | Max zone (mm) | LC value (µM) |
|---|---|---|---|
| Escherichia coli K12 | D21 | 18,3 | 0,3 |
| Escherichia coli | Bd2221/75 | 17,6 | 0,3 |
| Salmonella typhimurium | L12 | 15,2 | 1 |
| Proteus vulgaris | Pv11 | 3,5 | 300 |
| Pseudomones aeruginose | OT97 | 4,5 | 200 |
| Acinetobacter calcoaceticus | Ac11 | 12,5 | 3 |
| Bacillus megaterium | Bm11 | 17,4 | 0,3 |
| Bacillus subtilis | Bs11 | 10,3 | 15 |

We claim:

1. A bacteriocidal polypeptide which comprises a polypeptide consisting of the following amino acid sequence:

Arg-Arg-Arg-Pro-Arg-Pro-Pro-Tyr-Leu-Pro-Arg- Pro-Arg-Pro-Pro-Pro-Phe-Phe-Pro-Pro-Arg-Leu- Pro-Pro-Arg-Ile-Pro-Pro-Gly-Phe-Pro-Pro-Arg- Phe-Pro-Pro-Arg-Phe-Pro.

2. A polypeptide consisting of the amino sequence of claim 1.

3. A pharmaceutical composition containing as a bacteriocidal constituent a polypeptide according to claim 1 wherein said bacteriocidal polypeptide is contained in an amount sufficient to kill bacteria or to inhibit bacterial growth together with a pharmaceutically acceptable carrier or diluent.

4. A pharmaceutical composition according to claim 3, wherein said carrier or diluent is acceptable for oral, intramuscular, intravenous or subcutaneous administration.

5. A method for killing bacteria or inhibiting bacterial growth in a mammalian organism, comprising administering in an amount of a polypeptide according to claim 1 which is sufficient to kill bacteria or to inhibit bacterial growth in said mammalian organism.

6. A method according to claim 5 orally administering a composition containing said polypeptide in a slow release dose form together with a pharmaceutically acceptable carrier or diluent.

7. A method according to claim 5, comprising administering by injection a composition containing said polypeptide in an amount sufficient to kill bacteria or to inhibit the growth of bacteria in an injectable dose form together with a pharmaceutically acceptable carrier or diluent.

8. A pharmaceutical composition containing as a bacteriocidal constituent the polypeptide according to claim 2 wherein said polypeptide is contained in an amount sufficient to kill bacteria or to inhibit bacterial growth together with a pharmaceutically acceptable carrier or diluent.

9. A method for killing bacteria or inhibiting bacterial growth according to claim 5 wherein said mammalian organism is a human.

10. A method for killing bacteria or inhibiting bacterial growth in a mammalian organism, comprising administering a polypeptide according to claim 2 in an amount sufficient to kill bacteria or to inhibit bacterial growth.

11. A method for killing bacteria or inhibiting bacterial growth in a mammalian organism, comprising administering a composition according to claim 3 in an amount sufficient to kill bacteria or to inhibit bacterial growth.

12. A method for killing bacteria or inhibiting bacterial growth in a mammalian organism, comprising administering a composition according to claim 4 in an amount sufficient to kill bacteria or to inhibit bacterial growth.

* * * * *